Oct. 27, 1959 I. MACKAY Plant Pat. 1,875
CHRYSANTHEMUM PLANT
Filed Feb. 2, 1959
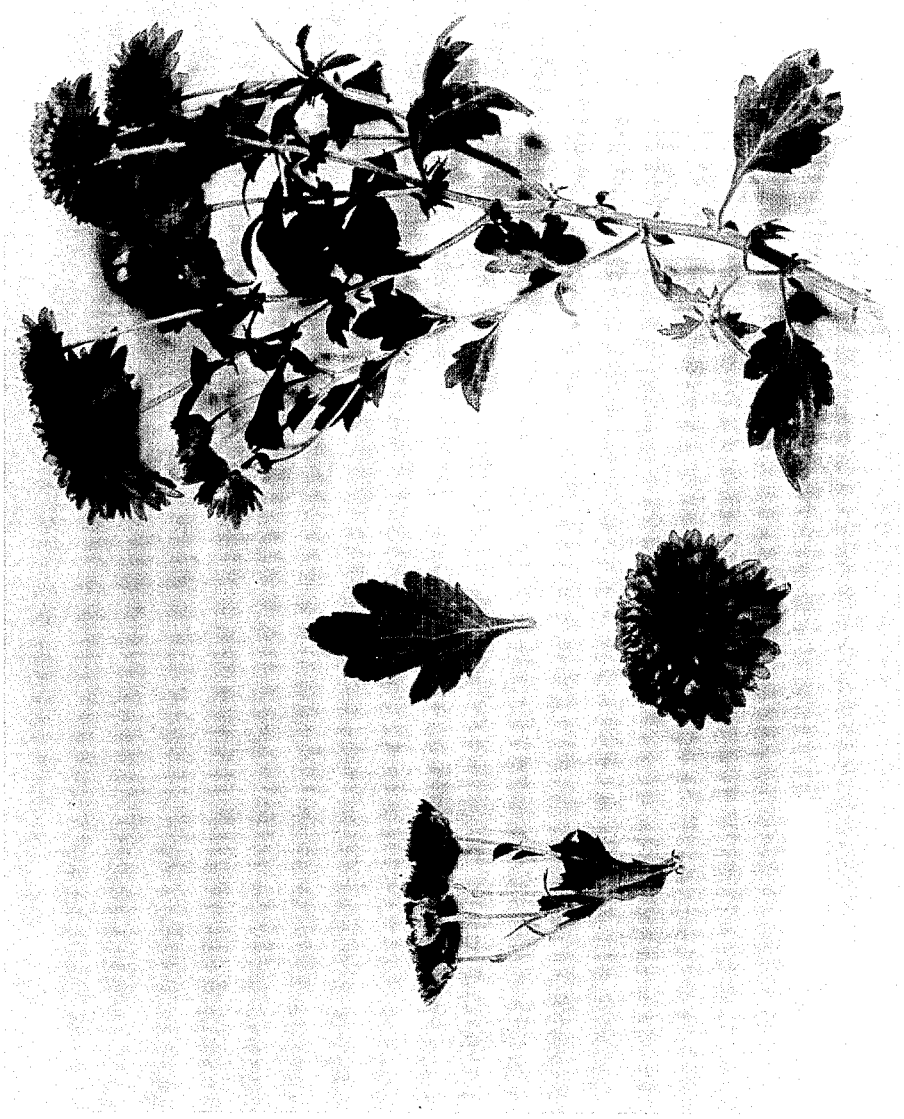
INVENTOR
Ian Mackay
BY Robb & Robb
ATTORNEYS United States Patent Office Plant Pat. 1,875
Patented Oct. 27, 1959

1,875

CHRYSANTHEMUM PLANT

Ian Mackay, Kirkwood, Pa., assignor to The Conard-Pyle Company, West Grove, Pa., a corporation of Pennsylvania Application February 2, 1959, Serial No. 790,403
1 Claim. (Cl. 47—60)

The present invention relates to a new and distinct variety of chysanthemum plant of the decorative cushion type, which was originated by me by crossing the variety "Maroon Cushion" (unpatented) with an unnamed and unpatented seedling.

The primary objective of this breeding was to produce a new chrysanthemum variety combining the Red color tonality of the parent variety "Maroon Cushion" with the large bloom size characteristic of the unnamed seedling parent, while at the same time combining the other better points of habit of both parents. This objective was fully achieved, along with other desirable improvements, as evidenced by the following characteristics which are outstanding in the new variety and which differentiate it from its parents as well as from all other varieties of its class of which I am aware:

(1) A compact habit of plant growth;
(2) Excellent floriferousness;
(3) A distribution of the blooms which gives an overall mass color effect;
(4) A very double flower form; and
(5) A Garnet Lake general color tonality of the flowers.

Asexual reproduction of the new variety by cuttings, as performed at West Grove, Pennsylvania, shows that the aforementioned characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious, as based upon observations made at West Grove, Pennsylvania:

Parentage: Seedling.
*Seed parent.*—"Maroon Cushion."
*Pollen parent.*—An unnamed seedling.
Type: Cushion; hardy; medium height; outdoor; seedling; for garden decoration.
Classification:
*Horticultural.*—Decorative.
*Botanical.*—Hortorum.
Propagation: Holds its distinguishing characteristics through succeeding propagations by cuttings.

*Flower*

Flowers borne: Several to stem; in pyramidal clusters; on stems of normal strength and medium length.
Quantity of bloom: Abundant, outdoors.
Continuity: Continuous during September and October.
Fragrance: Strong. Nature—chrysanthemum.

This description was made from a first year plant and bloom grown outdoors in the month of October at West Grove, Pennsylvania:

Bud:
*Peduncle.*—Medium length; slender; erect; rough; with numerous hairs. Color—Willow Green, Plate 000862.

*Before calyx breaks.*—Size—medium. Form—oval.
*As calyx breaks.*—Color—Chrysanthemum Crimson, Plate 824/2.
*As petals open.*—Color: inside—Garnet Lake, Plate 828; outside—Erythrite Red, Plate 0027/1.
*Opening.*—Opens up well; is not retarded from opening by any weather.

Bloom:
*Size (when fully open).*—Medium; 2½ inches in diameter.
*Form.*—Globular, with full center.
*Petalage.*—Fully double. Other petals straight; convex in transverse section. Inner petals—straight; concave in cross section.
*Color.*—Outer petals: inner surface—Garnet Lake, Plate 828; outer surface—between Erythrite Red, Plate 0027 and Erythrite Red, Plate 0027/1. Intermediate petals: inner surface—Garnet Lake, Plate 828; outer surface—between Erythrite Red, Plate 0027 and Erythrite Red, Plate 0027/1. Inner petals: inner surface—Garnet Lake, Plate 828; outer surface—between Erythrite Red, Plate 0027 and Erythrite Red, Plate 0027/1.
*Color change with age.*—None.

Ray flower petals: Medium thickness.
*Inside.*—Velvety.
*Outside.*—Shiny.
*Size.*—Outer—medium. Intermediate—medium. Inner—medium.
*Shape.*—Elliptic.

Disk flower petals: Few; medium size; medium length; medium thickness. Color—Canary Yellow, Plate 2.

Flower longevity:
*On bush in garden.*—Long duration.
*Cut flowers grown outdoors and kept at living-room temperatures.*—Medium duration.

*Genital organs*

Anthers: Few.
Stigma: Color—yellow.

*Plant*

Growth habit (as compared with other varieties grown simultaneously under the same cultural conditions in the field at West Grove, Pennsylvania): Bushy; much-branched; compact; attains a medium height and medium spread during the first year of growth, with the height usually greater than the spread.
Vigor: Free.
Stems: Color—Willow Green, Plate 000862.
Foliage: Medium size.
*Texture.*—Medium leathery.
*Upper surface.*—Rough; dull.
*Under surface.*—Hirsute.
*Quantity.*—Normal.
*Shape.*—Ovate, with apex acute.
*Base.*—Obtuse.
*Margin.*—Parted.
*Veins.*—Upper surface — medium prominence. Lower surface—prominent.
*Color.*—Upper side—Spinach Green, Plate 0960. Lower side—Lavender Green, Plate 000761.

I claim:

A new and distinct variety of chrysanthemum plant of the decorative cushion type, substantially as herein shown and described, characterized particularly as to novelty by the unique combination of a compact habit of plant growth, excellent floriferousness, a distribution of the blooms which gives an overall mass color effect, a very double flower form, and a Garnet Lake general color tonality of the flowers.

No references cited.